United States Patent [19]

Drabek

[11] Patent Number: 4,492,705
[45] Date of Patent: Jan. 8, 1985

[54] 3-AMIDINO-BENZISOTHIAZOLE-1,1-DIOXIDES AND THEIR USE FOR CONTROLLING PESTS

[75] Inventor: Jozef Drabek, Oberwil, Switzerland

[73] Assignee: Ciba-Geigy Corporation, Ardsley, N.Y.

[21] Appl. No.: 462,256

[22] Filed: Jan. 31, 1983

[30] Foreign Application Priority Data

Feb. 12, 1982 [CH] Switzerland ............ 888/82
Jan. 7, 1983 [CH] Switzerland ............ 87/83

[51] Int. Cl.³ .......................... C07D 275/06
[52] U.S. Cl. .................. 424/270; 548/212; 544/62; 544/106; 544/367; 546/202; 424/248.51; 424/267; 424/250
[58] Field of Search ........... 548/212; 544/62, 106, 544/367; 546/202; 424/270, 248.51, 267, 250

[56] References Cited

U.S. PATENT DOCUMENTS

| 2,751,392 | 6/1956 | Grogan et al. | 260/301 |
| 3,707,364 | 12/1972 | Becke et al. | 548/212 |
| 3,790,587 | 2/1974 | Boshagen et al. | 548/212 |
| 4,339,266 | 7/1982 | Levitt | 544/320 |

FOREIGN PATENT DOCUMENTS

| 0033984 | 8/1981 | European Pat. Off. | |
| 2803755 | 8/1979 | Fed. Rep. of Germany | 548/212 |
| 7329133 | 9/1973 | Japan | 548/212 |
| 8015965 | 1/1983 | Japan | 548/212 |

Primary Examiner—Donald G. Daus
Assistant Examiner—G. Hendricks
Attorney, Agent, or Firm—Frederick H. Rabin

[57] ABSTRACT

3-Amidino-benzisothiazole-1,1-dioxides of the formula

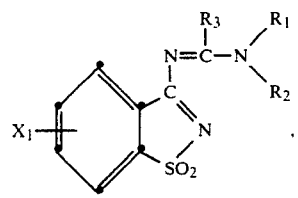

wherein
$R_1$ and $R_2$ are each $C_1$–$C_5$-alkyl or $C_2$–$C_5$-alkenyl,
$R_3$ is hydrogen or methyl, or
$R_1$ and $R_2$ together form a $C_3$–$C_6$-alkylene chain which can be interrupted by O, S or NH, or
$R_1$ and $R_3$ together are —$CH_2$—$CH_2$—$CH_2$—, and
$X_1$ is hydrogen, halogen, $C_1$–$C_5$-alkyl, halo-$C_1$–$C_5$-alkyl or $C_1$–$C_5$-alkoxy.

A process for producing these 3-amidino-benzisothiazole-1,1-dioxides and their use for controlling pests are described.

9 Claims, No Drawings

3-AMIDINO-BENZISOTHIAZOLE-1,1-DIOXIDES AND THEIR USE FOR CONTROLLING PESTS

The present invention relates to 3-amidino-benzisothiazole-1,1-dioxides, to processes for producing them and to their use for controlling pests.

The 3-amidino-benzisothiazole-1,1-dioxides have the formula I wherein
$R_1$ and $R_2$ are each $C_1$-$C_5$-alkyl or $C_2$-$C_5$-alkenyl,
$R_3$ is hydrogen or methyl, or
$R_1$ and $R_2$ together form a $C_3$-$C_6$-alkylene chain which can be interrupted by O, S or NH, or
$R_1$ and $R_3$ together are —CH$_2$—CH$_2$—CH$_2$— and
$X_1$ is hydrogen, halogen, $C_1$-$C_5$-alkyl, halo-$C_1$-$C_5$-alkyl or $C_1$-$C_5$-alkoxy.

By halogen is meant in this case fluorine, chlorine, bromine or iodine, especially however fluorine and chlorine.

The alkyl, haloalkyl, alkenyl or alkoxy groups denoted by $R_1$, $R_2$ and $X_1$ can be straight-chain or branched-chain. Examples of such groups are, inter alia: methyl, trifluoromethyl, methoxy, ethyl, ethoxy, propyl, propoxy, isopropyl, isopropoxy, n-, i-, sec- or tert-butyl, n-pentyl and isomers thereof, vinyl, 1-propenyl, 2-propenyl, isopropenyl, 3-butenyl or —CH$_2$—CH$_2$—CH=CH—CH$_3$. The preferred alkenyl group for $R_1$ and $R_2$ is 2-propenyl.

Examples of alkylene chains in the case of $R_1$ and $R_2$ are: propylene, butylene, pentylene and hexylene, which can be interrupted once or several times, particularly however once, by O, S or —NH. Preferred $R_1$ and $R_2$ alkylene chains are pentylene, —CH$_2$—CH$_2$—O—CH$_2$—CH$_2$—, —CH$_2$—CH$_2$—S—CH$_2$—CH$_2$— or —CH$_2$—CH$_2$—NH—CH$_2$—CH$_2$—.

Preferred compounds of the formula I are those wherein
$R_1$ and $R_2$ are each $C_1$-$C_5$-alkyl or $C_2$-$C_5$-alkenyl,
$R_3$ is hydrogen or methyl, or
$R_1$ and $R_2$ together form a $C_3$-$C_6$-alkylene chain which can be interrupted by O, S or NH, or
$R_1$ and $R_3$ together are —CH$_2$—CH$_2$—CH$_2$—, and
$X_1$ is hydrogen, halogen, $C_1$-$C_5$-alkyl or $C_1$-$C_5$-alkoxy.

Especially preferred compounds of the formula I are those wherein
$R_1$ and $R_2$ are each $C_1$-$C_4$-alkyl or 2-propenyl, or
$R_1$ and $R_2$ together are —CH$_2$—CH$_2$—CH$_2$—CH$_2$—CH$_2$—, —CH$_2$—CH$_2$—O—CH$_2$—CH$_2$—, —CH$_2$—CH$_2$—S—CH$_2$—CH$_2$— or —CH$_2$—CH$_2$—NH—CH$_2$—CH$_2$—,
$R_3$ is hydrogen, and
$X_1$ is hydrogen, halogen, methyl, trifluoromethyl or methoxy;
or compounds of the formula I wherein
$R_1$ and $R_2$ are each $C_1$-$C_4$-alkyl or 2-propenyl, or
$R_1$ and $R_2$ together are —CH$_2$—CH$_2$—CH$_2$—CH$_2$—CH$_2$—, —CH$_2$—CH$_2$—O—CH$_2$—CH$_2$—,
—CH$_2$—CH$_2$—S—CH$_2$—CH$_2$— or —CH$_2$—CH$_2$—NH—CH$_2$—CH$_2$—,
$R_3$ is hydrogen, and
$X_1$ is hydrogen, chlorine, methyl or methoxy.

More specifically preferred compounds of the formula I are those wherein
$R_1$ and $R_2$ are each methyl, n-butyl or 2-propenyl, or
$R_1$ and $R_2$ together are —CH$_2$—CH$_2$—CH$_2$—CH$_2$—CH$_2$— or —CH$_2$—CH$_2$—O—CH$_2$—CH$_2$—
$R_3$ is hydrogen, and
$X_1$ is hydrogen or chlorine;
or compounds of the formula I wherein
$R_1$ and $R_2$ are each methyl, n-butyl or 2-propenyl, or
$R_1$ and $R_2$ together are —CH$_2$—CH$_2$—CH$_2$—CH$_2$—CH$_2$— or —CH$_2$—CH$_2$—O—CH$_2$—CH$_2$, and
$R_3$ and $X_1$ are each hydrogen.

The compounds of the formula I are produced by methods known per se, for example as follows:

In the formulae II or VI, the symbols $R_1$, $R_2$, $R_3$ and $X_1$ have the meanings defined under the formula I, and R is $C_1$-$C_5$-alkyl, particularly methyl or ethyl. In the preferred benzisothiazoles of the formula II, $X_1$ is hydrogen, chlorine, methyl or methoxy, especially however hydrogen or chlorine. Examples of such benzisothiazoles are, inter alia: 3-aminobenzisothiazole-1,1-dioxide; 3-amino-4-chlorobenzisothiazole-1,1-dioxide; 3-amino-4-methylbenzisothiazole-1,1-dioxide and 3-amino-4-methoxybenzisothiazole-1,1-dioxide. In the preferred acetals of the formula III, $R_1$ and $R_2$ are each $C_1$-$C_4$-alkyl or 2-propenyl, or $R_1$ and $R_2$ together are —CH$_2$—CH$_2$—CH$_2$—CH$_2$—CH$_2$—, —CH$_2$—CH$_2$—O—CH$_2$—CH$_2$—, —CH$_2$—CH$_2$—S—CH$_2$—CH$_2$— or —CH$_2$—CH$_2$—NH—CH$_2$—CH$_2$—, $R_3$ is hydrogen, and R is ethyl. Examples of such acetals are, inter alia: dimethylformamide-diethylacetal and di-n-butylformamide-diethylacetal, as well as acetals of the formulae

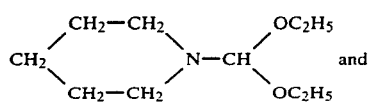

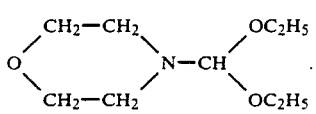

The processes are performed under normal pressure, at a temperature of 0° to 160° C., preferably at 60° to 140° C., and optionally in a solvent or diluent. Suitable solvents or diluents are for example: ethers and ethereal compounds, such as diethyl ether, diisopropyl ether, dioxane or tetrahydrofuran; aliphatic and aromatic hydrocarbons, especially benzene, toluene or xylenes; ketones, such as acetone, methyl ethyl ketone and cyclohexanone.

The starting materials of the formulae II to V are known, and can be produced by methods analogous to known methods. Thus the process for producing preferred benzisothiazoles of the formula II is described in the European patent application No. 00 33984 and in the Japanese patent application No. 73/24735, and for producing acetals of the formula III in Liebigs Annalen der Chemie 641, 1, 1961.

The compounds of the formula I are suitable for controlling pests on animals and plants.

These compounds of the formula I are particularly suitable for controlling insects, for example of the orders: Lepidoptera, Coleoptera, Homoptera, Heteroptera, Diptera, Thysanoptera, Orthoptera, Anoplura, Siphonaptera, Mallophage, Thysanura, Isoptera, Psocoptera and Hymenoptera; and also mites and ticks of the order Acarina.

The compounds of the formula I are especially suitable for controlling insects that damage plants, in particular insects that damage plants by eating, in crops of ornamental plants and productive plants, particularly in cotton crops (for example against *Spodoptera littoralis* and *Heliothis virescens*); and also in vegetable crops (for example against *Leptinotarsa decemlineata* and *Myzus persicae*); and in rice crops (for example against *Chilo suppressalis*, Laodelphax).

It is to be emphasized in this connection that the said compounds are distinguished by both a strongly pronounced systemic action and contact action against sucking insects, especially against sucking insects of the order Homoptera, and above all against insects of the family Aphididae (for example *Aphis fabae, Aphis craccivora* and *Myzus persicae*), which can be controlled with known compositions only with great difficulty.

Active substances of the formula I exhibit also a very good action against flies, for example Musca domestica, and against mosquito larvae, as well as against ectoparasitic mites and ticks, for example of the families: Ixodidae, Argasidae and Dermanyssidae. Furthermore, the compounds of the formula I are characterised by a broad ovicidal and ovilarvicidal action.

In addition, the compounds of the formula I have fungicidal properties and properties for regulating plant growth; and they also have a valuable action against phytoparasitic nematodes.

The compounds of the formula I are used either in an unmodified form or preferably together with auxiliaries customarily employed in formulation practice, and are thus processed in a known manner for example into the form of emulsion concentrations, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or parrafins, alcohols and glycols, as well as ethers and esters thereof, such as ethanol, ethylene glycol, ethylene glycol monomethyl or -ethyl esters, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example, pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I to be formulated, nonionic, cationic and/or anionic tensides having good emulsifying, dispersing and wetting properties. By 'tensides' are also meant mixtures of tensides.

Suitble anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$-$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsufuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenyl-(4-14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylene-diaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenol-polyethoxyethanols, castor oil polyglycol ethers, polypropylene/polyethyleneoxy adducts, tributylphenoxy-polyethoxyethanol, polyethylene glycol and octylphenoxy-polyethoxyethanol. Suitable also are fatty acid esters of polyoxyethylenesorbitan, such as polyoxythylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammoniumchloride or benzyldi(2-chloroethyl)ethylammonium bromide.

The tensides customarily used in formulation practice are described, inter alia, in the following publication:

"Mc Cutcheon's Detergents and Emulsifiers Annual", MC Publishing Corp., Ringwood, N.J., 1979.

The pesticidal preparations contain as a rule 0.1 to 99%, particularly 0.1 to 95%, of active ingredient of the formula I, 1 to 99.9% of a solid or liquid additive, and 0 to 25%, especially 0.1 to 25%, of a tenside. Whereas commercial products are preferably in the form of concentrated compositions, the compositions employed by the end-user are as a rule diluted.

The compositions can also contain additives such as stabilisers, antifoam agents, viscosity regulators, binders and adhesives, as well as fertilisers or other active substances for obtaining special effects.

Ready-for-use dusts are obtained by the intimate mixing together of the carriers with the active ingredient.

Formulation Examples for active ingredients of the formula I (%=percent by weight)

| 1. Wettable powders | (a) | (b) | (c) |
|---|---|---|---|
| active ingredient | 25% | 50% | 75% |
| sodium lignin sulfonate | 5% | 5% | — |
| sodium lauryl sulfate | 3% | — | 5% |
| sodium diisobutylnaphthalene | — | 6% | 10% |

| 1. Wettable powders -continued | (a) | (b) | (c) |
|---|---|---|---|
| sulfonate | | | |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of the required concentration are obtained.

| 2. Emulsion concentrate | |
|---|---|
| active ingredient | 10% |
| octylphenolpolyethylene glycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| 3. Dusts | (a) | (b) |
|---|---|---|
| active ingredient | 5% | 8% |
| talcum | 95% | — |
| kaolin | — | 92% |

Dusts ready for use are obtained by mixing the active ingredient with the carriers and grinding the mixture in a suitable mill.

| 4. Extruder granulate | |
|---|---|
| active ingredient | 10% |
| sodium lignin sulfonate | 2% |
| carboxymethylcellulose | 1% |
| kaolin | 87% |

The active substance is mixed and ground with the additives, and the mixture is moistened with water. This mixture is extruded and then dried in a stream of air.

| 5. Coated granulate | |
|---|---|
| active ingredient | 3% |
| polyethylene glycol (MG 200) | 3% |
| kaolin | 94% |

The finely ground active ingredient is evenly applied, in a mixer, to the kaolin moistened with polyethylene glycol. Dustfree coated granules are obtained in this manner.

| 6. Suspension concentrate | |
|---|---|
| active ingredient | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |

| | -continued | |
|---|---|---|
| 6. Suspension concentrate | | |
| water | | 32% |

The finely ground active ingredient is intimately mixed with the additives. There is thus obtained a suspension concentrate from which can be produced, by dilution with water, suspensions of the concentration required.

EXAMPLE 1

Production of the compound No. 1 of the formula 2.6 g of 3-amino-benzisothiazole-1,1-dioxide are mixed together with 7 ml of dimethylformamide-diethylacetal, and the mixture is held, with stirring, for 5 hours at 120° C. The product after cooling is filtered off with suction, washed with ether on the suction filter, and dried at 20° C. There is thus obtained the compound No. 1 having a melting point of 233° C.

The following compounds are produced in an analogous manner:

| No. | $R_1$ | $R_2$ | $R_3$ | X' | X'' | X''' | $X^{IV}$ | Physical data |
|---|---|---|---|---|---|---|---|---|
| 2. | $-C_4H_{9(n)}$ | $-C_4H_{9(n)}$ | H | H | H | H | H | m.p.: 109–110° C. |
| 3. | $-CH_2-CH=CH_2$ | $-CH_2-CH=CH_2$ | H | H | H | H | H | m.p.: 133° C. |
| 4. | $-CH_2-CH_2-2-CH_2-CH_2-$ | | H | H | H | H | H | m.p.: 225–227° C. |
| 5. | $-CH_2-CH_2-O-CH_2-CH_2-$ | | H | H | H | H | H | m.p.: 203° C. |
| 6. | $-C_2H_5$ | $-C_2H_5$ | H | H | H | H | H | resin |
| 7. | $-CH_3$ | $-CH_3$ | $-CH_3$ | H | H | H | H | m.p.: 170–175° C. |
| 8. | $-CH_3$ | $-CH_3$ | H | Cl | H | H | H | m.p.: 240–245° C. |
| 9. | $-CH_3$ | $-CH_3$ | $-CH_3$ | Cl | H | H | H | m.p.: 178–182° C. |
| 10. | $-C_4H_{9(n)}$ | $-C_4H_{9(n)}$ | H | Cl | H | H | H | m.p.: 102–103° C. |
| 11. | $-CH_2-CH_2-CH_2-CH_2-CH_2-$ | | H | Cl | H | H | H | m.p.: 215–217° C. |
| 12. | $-CH_2-CH_2-O-CH_2-CH_2-$ | | H | Cl | H | H | H | m.p.: 228–230° C. |
| 13. | $-CH_2-CH=CH_2$ | $-CH_2-CH=CH_2$ | H | Cl | H | H | H | m.p.: 157–158° C. |

EXAMPLE 2

Insecticidal contact action: *Aphis craccivora*

Plants (*Vicia fabae*) grown in pots are each infested before commencement of the test with about 200 individuals of the species *Aphis craccivora*. The plants infested in this manner are sprayed dripping wet 24 hours later with solutions containing 200 to 100 ppm, respectively, of the compound to be tested. Two plants are used per test compound and per concentration, and an evaluation of the mortality rate achieved is made after a further 24 hours.

The compounds according to Example 1 exhibit in the above test, against insects of the species *Aphis craccivora*, the level of activity shown in the Table which follows.

EXAMPLE 3

Systemic insecticidal action: *Aphis craccivora*

Rooted bean plants are transplanted to pots each containing 600 ccm of soil; and 50 ml of a solution of the compound to be tested (obtained from a 25% wettable powder) at a concentration of 50 ppm and 12.5 ppm, respectively, are subsequently poured directly onto the soil in each case. After 24 hours, aphids of the species *Aphis craccivora* are settled onto the parts of the plants above the soil, and a plastics cylinder is placed over each plant and drawn to by tying at the bottom in order to protect the aphids from any contact or gas action of the test substance. An evaluation of the mortality rate is achieved is made 48 and 72 hours after commencement of the test. Two plants, each in a separate pot, are used per concentration level of test substance. The test is carried out at 25° C. with 70% relative humidity.

The compounds according to Example 1 exhibit in the above test, against insects of the species *Aphis craccivora*, the systemic activity shown in the following Table.

Biological test results

In the following Table are summarised test results based on the Examples given in the foregoing, the index of values with regard to the percentage mortality of the pests being as follows:

| | | |
|---|---|---|
| A: | 70–100% mortality with 12.5 | ppm of active ingredient; |
| B: | 70–100% mortality with 50 | ppm of active ingredient; |
| C: | 70–100% mortality with 100 | ppm of active ingredient; |
| D: | 70–100% mortality with 200 | ppm of active ingredient. |

| Compound No. | Contact action against *Aphis craccivora* | Systemic action against *Aphis craccivora* |
|---|---|---|
| 1 | C | A |
| 2 | C | A |
| 3 | C | A |
| 4 | D | B |
| 5 | D | B |
| 6 | D | B |
| 7 | D | B |
| 8 | C | A |
| 9 | D | A |
| 10 | C | A |
| 11 | C | B |
| 12 | C | B |

What is claimed is:

1. 3-Amidino-benzisothiazole-1,1-dioxide of the formula I

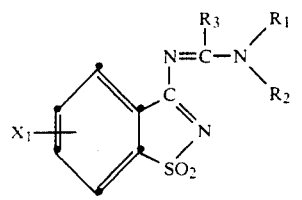
(1)

wherein
R$_1$ and R$_2$ are each C$_1$-C$_5$-alkyl or C$_2$-C$_5$-alkenyl,
R$_3$ is hydrogen or methyl, or
R$_1$ and R$_2$ together form a C$_3$-C$_6$-alkylene chain which can be interrupted by O, S or NH, or
R$_1$ and R$_3$ together are —CH$_2$—CH$_2$—CH$_2$—, and
X$_1$ is hydrogen, halogen, C$_1$-C$_5$-alkyl, halo-C$_1$-C$_5$-alkyl or C$_1$-C$_5$-alkoxy.

2. A compound according to claim 1, wherein X$_1$ is hydrogen, halogen, C$_1$-C$_5$-alkyl or C$_1$-C$_5$-alkoxy.

3. A compound according to claim 1, wherein R$_1$ and R$_2$ are each C$_1$-C$_4$-alkyl or 2-propenyl, or R$_1$ and R$_2$ together are —CH$_2$—CH$_2$—CH$_2$—CH$_2$—CH$_2$—, —CH$_2$—CH$_2$—O—CH$_2$—CH$_2$—, —CH$_2$—CH$_2$—S—CH$_2$—CH$_2$— or —CH$_2$—CH$_2$—NH—CH$_2$—CH$_2$—, R$_3$ is hydrogen, and X$_1$ is hydrogen, halogen, methyl, trifluoromethyl or methoxy.

4. A compound according to claim 3, wherein X$_1$ is hydrogen, chlorine, methyl or methoxy.

5. A compound according to claim 4, wherein R$_1$ and R$_2$ are each methyl, n-butyl or 2-propenyl, or R$_1$ and R$_2$ together are —CH$_2$—CH$_2$—CH$_2$—CH$_2$—CH$_2$— or —CH$_2$—CH$_2$—O—CH$_2$—CH$_2$—, and X$_1$ is hydrogen or chlorine.

6. A compound according to claim 5, wherein X$_1$ is hydrogen.

7. The compound according to claim 6 of the formula

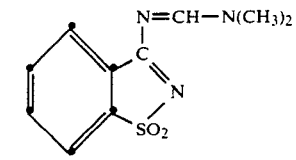

8. An insecticidal and acaricidal composition which contains (1) as active ingredient a compound according to claim 1, and (2) an inert auxiliary material.

9. A method for controlling insects and acarides which comprises applying thereto or to the locus thereof and insecticidally or acaricidally effective amount of a compound according to claim 1.

* * * * *